United States Patent [19]

Serimian et al.

[11] Patent Number: Plant 6,544

[45] Date of Patent: Jan. 17, 1989

[54] NECTARINE TREE, "SUMMER LION — TWO"

[76] Inventors: Donald M. Serimian, 2961 McCall Ave.; Lionel M. Serimian, 11310 E. Manning, both of Selma, Calif. 93662

[21] Appl. No.: 120,499

[22] Filed: Nov. 13, 1987

[51] Int. Cl.[4] ..... A01H 5/00

[52] U.S. Cl. ..... Plt./41

[58] Field of Search ..... Plt./41

*Primary Examiner*—Robert E. Bagwill

*Attorney, Agent, or Firm*—Worrel & Worrel

[57] ABSTRACT

A new and distinct variety of nectarine tree which is somewhat similar to the May Grand Nectarine Tree (U.S. Plant Pat. No. 2,794), and the Red Lion Nectarine Tree (U.S. Plant Pat. No. 5,591) with which it is most closely related but which it is distinguished therefrom by producing fruit which are mature for commercial harvesting approximately July 10 through July 19 and which further produces a very large, globose shaped fruit having a freestone nature and which exhibits a dark burgundy red to a lighter cherry red skin color, a clear amber-yellow colored flesh and has excellent eating qualities.

1 Drawing Sheet

BACKGROUND OF THE NEW VARIETY

The present invention relates to a new and distinct variety of nectarine tree which has been denominated varietally as "Summer Lion — Two", and more particularly to such a nectarine tree which is mature for commercial harvesting from approximately July 10 to July 19, the date of harvesting being approximately five days after the Summer Grand Nectarine Tree (U.S. Plant Pat. No. 2,879) with which it is somewhat closely similar in its date of harvesting, and which is further distinguished as to novelty by producing a freestone fruit whose flesh is firm, and crisp, and has a clear amber-yellow color; and which further produces fruit which have a very large size, a globose shape and which possess an aromatic and distinctive flavor.

From an economic standpoint, the relative dates of ripening of various varieties of nectarine trees is of extreme importance. It has long been recognized as desirable to have the harvesting periods of various nectarine trees effectively spread over longer periods of time. This results in considerable savings and increased efficiency because the capitol expenditures required to harvest and transport the fruit produced by these trees can be spread over a longer period of time, resulting in lower cost of the final product and increasing the uniformity of production.

It has long been known that the purchase of fruit products such as nectarines, by consumers, is largely influenced by the more noteworthy characteristics of the fruit, that is, the fruit size, the exterior coloration, and its eating quality. Thus, it has been recognized that it is desirable to provide a nectarine tree bearing fruit having the commercially aesthetic appeal of fruit such as that presented by the present invention. The fruit of the subject variety is noteworthy in that it produces fruit which have a very large size, a highly attractive skin color of dark burgundy red, (6-L-9) to a lighter cherry red (4-L-10), and a superior globose shape.

ORIGIN AND ASEXUAL REPRODUCTION OF THE NEW VARIETY

The present variety of nectarine tree is the product of a successful cross pollination of a May Grand Nectarine Tree (U.S. Plant Pat. No. 2,794) with a Red Lion Nectarine Tree (U.S. Plant Pat. No. 5,591); the cross pollination procedure being performed by the applicants in the spring of 1983 at the applicants' orchard which is located at 11024 East Dinuba Avenue, Selma, Calif. Following this cross pollination, seeds were produced, and were later germinated. Bud wood was removed from the resultant plants in 1984, and was grafted onto test nectarine trees which were located in the applicant's test block at the same orchard. The fruit produced were studied and it was subsequently determined that they exhibited desirable traits. After appreciating the excellent qualities of the subject variety, the applicants thereafter asexually reproduced the instant variety by budding it onto stock nectarine trees in 1985. The budded progeny were grown at the applicants' same orchard until it was determined that the new variety dependably and accurately reproduced the superior characteristics observed by the applicants in the original seedling.

SUMMARY OF THE NEW VARIETY

The Summer Lion — Two Nectarine Tree is characterized by many of the desirable features found in the May Grand Nectarine Tree (U.S. Plant Pat. No. 2,794) and the Red Lion Nectarine Tree (U.S. PlantPat. No. 5,591) but has the important distinction of bearing fruit which is mature for commercial harvesting approximately five weeks later than the May Grand Nectarine Tree, and approximately one month earlier than the Red Lion Nectarine Tree. Furthermore, the Summer Lion-Two Nectarine Tree produces a very large, high colored fruit which is of excellent quality, has a pleasing globose shape, and is freestone in nature. Moreover, the fruit of the Summer Lion-Two ripens about five days after the Summer Grand Nectarine Tree (U.S. Plant Pat. No. 2,879), the Summer Grand Nectarine being a high volume, mid-season nectarine which matures at approximately the same time of the season, but is distinguished therefrom by producing fruit which has a somewhat darker burgundy red blush than that produced by the Summer Grand Nectarine Tree, and is substantially larger in size. In addition to the foregoing, the fruit of the Summer Lion — Two Nectarine Tree has a more globose fruit shape than that of the Summer Grand Nectarine Tree and has an aromatic and distinctive flavor which places it among the very best of mid-season nectarines.

BRIEF DESCRIPTION OF THE DRAWINGS

The drawing is a color photograph of three mature fruit characteristic of the instant variety, two of the fruit display skin colorations which are sufficiently mature for harvesting and shipment; another fruit has been halved along the axial plane thereby exposing the flesh coloration of a typically mature fruit; the drawing also shows a typical twig bearing characteristic leaves which display the ventral and dorsal coloration thereof, together with two typical stones, all of the subject variety.

DETAILED DESCRIPTION

Referring more particularly to the specific pomological details of this new and distinct variety of nectarine tree, the following observations were made under the ecological conditions common to the applicants' orchard which is located at 11024 East Dinuba, Avenue, Selma, Calif. The Dictionary of Color by Maerz and Paul, Second Edition, published in 1950 is the source of all major color code designations. Common color names are also used occasionally.

TREE

Size:
- *Generally.*—average.

Vigor: Vigorous; hardy when grown under typical San Joaquin Valley climatic conditions.

Figure: Upright with density and form determined by pruning practices.

Trunk:
- *Thickness.*—average.
- *Surface texture.*—average.
- *Bark color.*—gray-brown, (7-C-10).
- *Lenticels.*—many large lenticels are present; brown callouses (13-I-9) appear next to the lenticel opening.

Branches:
- *Size — mature branches.*—average.
- *Surface texture — mature branches.*—average.
- *Color — mature branches.*—brown, (15-H-10).
- *Size — immature branches.*—average.
- *Color — immature branches.*—light green, (18-H-5).
- *Surface texture — immature branches.*—smooth.

LEAVES

Size: Large, with an average length of approximately 19.9 cm.; and an average width of approximately 5.4 cm.

Form: Broadly lanceolate with an acuminate tip; the leaves frequently appear twisted.

Color:
- *Dorsal surface.*—a dark green (24-L-3).
- *Ventral surface.*—a light gray green (21-G-4). A distinctive leaf vein is evident when viewed from the ventral side of the leaf. The leaf vein is approximately 1.0 mm. wide at the center of the leaf, and is a light yellow-green in color, (17-H-3).

Margin: Crenate; the crenations are very fine and regular. The margins are slightly undulate.

Petiole:
- *Size.*—medium.
- *Length.*—generally — average, approximately 13 to 15 mm.
- *Thickness.*—approximately 2.0 mm.
- *Color.*—light green, (17-I-3).

Glands:
- *Form.*—variable — predominantly reniform, although occasionally globose types may be evident.
- *Location.*—two to three typically appear on the upper petiole and one or two usually appear on the basal portion of the leaf margin.
- *Gland pattern.*—alternate.
- *Gland color.*—a light green-yellow, (17-K-2); the glands are shiny when immature but darken with advancing maturity.

Stipules:
- *Generally.*—two stipules are evident, these typically subtend the leaf petiole.
- *Color.*—light green, (17-H-5), the stipules have dark margins. Early deciduous.

FLOWERS

Generally: The flowers of the subject variety are not particularly distinctive.

Blooming time: Mid-season to slightly late in relation to other common nectarine varieties growing in this geographical area.

Flower size: Large and showy in form.

Bloom amount: Average.

Flower buds and scales:
- *Bud size.*—average for the species; pubescent.
- *Bud form.*—conic.
- *Buds produced per node.*—one to two.
- *Petal size.*—large.
- *Petal form.*—ovate.
- *Petal color.*—light pink (1-E-2). Petals darken with maturity.
- *Pedicle.*—length — very short.
- *Nectaries.*—color — orange (11-J-11); this portion of the plant darkens with advancing maturity.
- *Anthers.*—size — small.
- *Stamens.*—length — variable, however, the stamens are usually shorter than the pistil.
- *Pistil position.*—usually above the anthers when fully extended.
- *Pistil texture.*—glabrous.
- *Pistil color.*—yellow-green (17-H-3).

FRUIT

Maturity when described: Ripe for commercial harvesting and shipment; July 10, 1987 was the date of first pick in Fresno County, Calif. The date of last pick was July 19, 1987.

Size: Very large and uniform. Average cheek diameter-approximately 79.5 mm.; average suture diameter-approximately 80.3 mm.; average axial diameter-approximately 79.5 mm.

Form: Uniform; only very slightly asymmetrical; globose to very slightly ovate laterally; and uniformly globose apically.

Suture:
- *Generally.*—the suture color commonly matches the underlying blush color with occasional fine streaking of red appearing on some fruit; this occasional streaking is usually darker than the general shade of the suture. The suture appears as a shallow but distinct depression which extends from the apex to the base, although the suture is slightly deeper over the apical shoulder up to the apex. Most fruit have a moderate depression on the suture line on both sides of the apex.

Ventral surface: Commonly smooth and rounded with a slight amount of lipping being evident around the apical shoulder area of the ventral suture.

Stem cavity:

*Generally.*—oval, and moderately deep and narrow with the cavity being approximately 30 to 31 mm. wide, 32 to 35 mm. long, and 14 to 18 mm. deep. Frequently there is an indentation formed in the fruit where it was attached to the bearing limb.

Base:

*Form.*—rounded to slightly truncate. Commonly the base isat a substantially right-angle with respect to the fruit axis, or at only a slightly oblique angle with respect thereto.

Apex:

*Shape.*—rounded and very low; the height varies from slightly above the apical shoulder to slightly below the apical shoulder. The pistil point is also variable from apical to oblique. The apex is commonly subtended by depressions which appear on both ventral and dorsal sutures.

Stem:

*Color.*—a light green-yellow (18-K-2).

*Average thickness.*—approximately 3.5 to 4.5 mm.

*Average length.*—approximately 11 to 14 mm.

Skin:

*Generally.*—glabrous; tenacious to flesh at commercial maturity; no observed tendency to crack; average thickness; mild in flavor.

Skin color:

*Generally.*—the variety displays a full to 90% blush color. The blush color is variable from a dark burgundy red (6-L-9), to a lighter cherry red (4-L-10), with a wide variety of shades therebetween. A small amount of ground color is visible generally around the stem cavity or over the basal end of the fruit. The ground color is yellow (10-K-4).

Flesh color:

*Generally.*—a clear amber-yellow (10-K-5) from the skin to the pit cavity with no red flecking evident in the flesh. The pit cavity is red on the surface, (5-L-9), with some red rays extending 3 to 8 mm. into the flesh.

Flesh texture: At commercial maturity, the flesh of the subject variety is crisp and firm, the flesh becomes juicy and melting with advancing maturity.

Flesh fibers:

*Length.*—short.

*Texture.*—fine and tender; numbers — average.

Ripening: Even.

Flavor: Very good; pleasant and well balanced.

Aroma: Moderate, very pleasant and mild.

Overall eating quality: Excellent.

STONE

Attachment: Freestone. The stone of the subject variety breaks away cleanly from the flesh with only a few fibers clinging to the basal area of the dorsal and ventral suture.

Size:

*Generally.*—large; approximately 42 to 44 mm. in length; 29 to 31 mm. in width; and 23 to 24 mm. in thickness.

Fibers:

*Generally.*—a few fibers of medium length are evident; the fibers are attached on the dorsal and ventral suture areas.

Form: Obovate, occasionally strongly so.

Base:

*Form.*—broadly truncate with the base angle being slightly oblique to the fruit axis.

Hilum:

*Generally.*—large and roughly oval; the hilum is heavily eroded.

Apex:

*Shape.*—usually rounded with a small sharp acuminate tip.

Sides:

*Form.*—variable, usually unequal.

Surface:

*Texture.*—moderately rough and having an average number of deep grooves over the apical shoulders. Grooves also appear near the ventral suture and converge basally. Irregularly shaped pits occur laterally over the mid-stone area.

Dorsal edge:

*Generally.*—a coarse and moderately wide suture is evident; significant erosion is apparent in the apical shoulder area. A moderately wide groove extends from the base to approximately 10 to 15 mm. below the apex. A prominent area frequently protrudes along the suture and is positioned about 15 mm. below the apex.

Ventral edge:

*Generally.*—the stone of the subject variety displays an average suture width with very low wings along the entire length of the suture.

Stone color: A medium brown, (13-G-8); a red-purple stain is visible on most stones, this coloration is most evident basally.

Tendency to split: Not observed.

Use: Fresh market for both local and long distance markets.

Keeping quality: Good.

Shipping quality: The subject variety has not yet been shipped in volume, however, the firm crisp flesh at commercial maturity strongly indicates that the variety will have noteworthy characteristics.

Although the new variety of nectarine tree possesses the desired characteristics as a result of the growing conditions prevailing in Fresno County, Calif., in the central San Joaquin Valley, it is to be understood that variations in the usual magnitude and characteristics incident to growing conditions, fertilization, pruning and pest control are to be expected.

Having thus described and illustrated our new variety of Nectarine Tree, what is claimed as new and desired to be secured by Plant Letters Patent is:

1. A new and distinct variety of nectarine tree substantially as illustrated and described which is somewhat similar to the May Grand Nectarine Tree (U.S. Plant Pat. No. 2,794), and the Red Lion Nectarine Tree (U.S. Plant Pat. No. 5,591) from which it was derived as a cross pollinated seedling but from which it is distinguished therefrom and characterized as to novelty by producing fruit which are mature for commercial harvesting approximately July 10 through July 19 in the San Joaquin Valley of central California and which additionally produces a very large globose shaped fruit which has a freestone nature, a dark burgundy red to a lighter cherry red skin color and a flesh color which is clear amber-yellow; the fruit of the subject variety having excellent eating qualities.

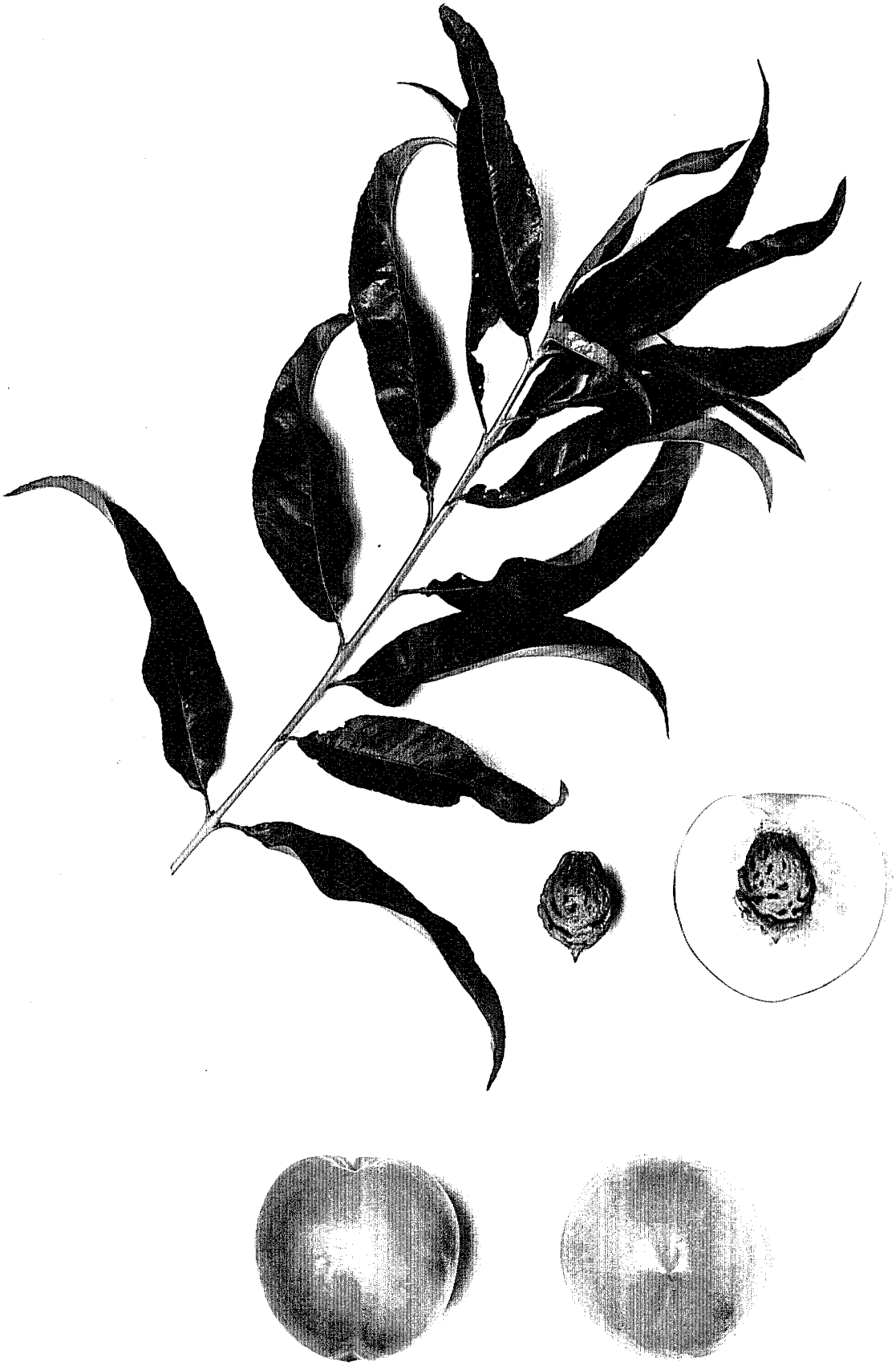

* * * * *